United States Patent [19]

Parr

[11] Patent Number: 4,538,000
[45] Date of Patent: Aug. 27, 1985

[54] NON-IONIC UNSATURATED CHEMICAL COMPOUNDS

[75] Inventor: Rodney W. Parr, Doncaster, Australia

[73] Assignee: Dulux Australia Ltd., Melbourne, Australia

[21] Appl. No.: 554,104

[22] Filed: Nov. 21, 1983

[30] Foreign Application Priority Data

Dec. 3, 1982 [AU] Australia .............................. PF7102

[51] Int. Cl.³ .............................................. C07C 43/15
[52] U.S. Cl. .................................. 568/616; 568/608; 252/351
[58] Field of Search ................................ 568/608, 616

[56] References Cited

PUBLICATIONS

Tsuji et al, Chemical Abstracts, 48 (1954), 14134a.

Primary Examiner—Bernard Helfin
Attorney, Agent, or Firm—Cushman, Darby & Cushman

[57] ABSTRACT

There are disclosed non-ionic unsaturated chemical compounds having both hydrophilic and lipophilic components.

The hydrophilic component comprises at least two ethylene oxide units and the lipophilic component has a molecular weight of 1000 maximum and comprises an entity selected from eugenol, pentaerythritol triallyl ether and trimethylolpropane diallyl ether.

The compounds are useful, for example, as emulsion stabilizers.

2 Claims, No Drawings

NON-IONIC UNSATURATED CHEMICAL COMPOUNDS

This invention relates to novel non-ionic chemical compounds having both hydrophilic aqnd lipophilic components and more particularly to those comprising ethylenic double bonds.

Non-ionic chemical compounds having both hydrophilic (water-soluble or solvatable) components and lipophilic (oil soluble or solvatable) components (hereinafter referred to as "two component compounds") have been known for many years and have been used widely in a great variety of applications. One very well known class of two component compounds is that of the non-ionic surfactants; such compounds are widely used in the preparation and stabilisation of emulsions for all kinds of applications. Non-ionic surfactants and their uses are comprehensively described in the standard text "Emulsions: Theory and Practice" by P. Becher (2nd Ed., Reinhold, 1966). A related class of materials is that of the amphipathic stabilisers used in the preparation and stabilisation of non-aqueous dispersions; such compounds are described in the reference work "Dispersion Polymerization in Organic Media" (K. E. J. Barrett ed., Wiley, 1975). In both of these cases, the sizes of the two components must be carefully adjusted in both absolute and relative senses.

There is also known a class of two component compounds which comprise ethylenic double bonds. These can be used as comonomers in polymerisation processes when it is desired that the final polymer be water-dispersible. Suitable compounds of this clas can also be used as surfactants. For example, in European Published Application No. 0 002 252, a two component compound comprising at least two allyl groups acts as a surfactant for a dispersion of an alkyd resin in water. On coalescence and film formation, the allyl double bonds participate in the autoxidation reaction and any potential surfactant-created water sensitivity is thus removed. Other examples of two component compounds may be found in, for example, U.S. Pat. No. 4,229,547 and in the work of Rao et al (see "Chemical Abstracts", 89 131488a).

I provide, according to the present invention, a novel non-ionic chemical compound having both hydrophilic and lipophilic components, the hydrophilic component comprising a polyalkylene oxide chain and the lipophilic component comprising at least one ethylenic double bond, characterised in that
 (a) the hydrophilic component comprises at least two ethylene oxide units,
 (b) the lipophilic component has a molecular weight of 1000 maximum and comprises an entity derived from an unsaturated compound selected from the group consisting of eugenol, pentaerythritol triallyl ether and trimethylolpropane diallyl ether.

The hydrophilic components of the two component compounds of this invention are comprised of alkylene oxide units, at least two of which must be ethylene oxide units. As the hydrophillic component must remain hydrophilic, the choice of numbers and natures of alkylene oxide units must be made carefully. In practice, this means that in a two component compound according to the invention, the hydrophilic component will comprise a relatively large proportion of water-soluble ethylene oxide units and a relatively small proportion of other alkylene oxide units such as propylene and butylene oxides which tends to reduce hydrophilicity.

The lipophilic component must have a maximum molecular weight of 1000 and must comprise an entity derived from an unsaturated compound selected from the group consisting of eugenol, pentaerythritol triallyl ether trimethylolpropane diallyl ether. In one preferred case, the entire lipophilic component is comprised of such an entity but it is possible for the lipophilic component to comprise other species. It is not necessary that such species be lipophilic per se; they may in fact be hydrophilic, provided that the overall lipophilicity of the lipophilic component is maintained. For example, an example of an acceptable lipophilic component comprises pentaerythritol triallyl ether and two units of butylene oxide, the two being linked by an ethylene oxide unit.

It is of course possible and permissible to have other water-insoluble species attached to the unsaturated compound. Such species may be chosen from the wide variety of suitable species known to the art, provided that the overall molecular weight limit is not exceeded and that they do not impart undesirable properties bearing in mind the end use to which the two component compound will be put.

The two component compounds of this invention have a variety of uses. They can, for example, be used as emulsion stabilisers, either for water-in-oil (W/O) or oil-in-water (O/W) emulsions. The suitability for these tasks is largely determined by the hydrophile-lipophile balance (HLB) value of the compound. This important parameter of surface-active agents and the methods of determining it are well known to manufacturers and users of such agents. If the two component compounds of our invention have HLB values of from about 4–10, the compounds are useful as W/O stabilisers. Compounds with HLB values of from about 8 upwards are useful as O/W stabilisers; these compounds have been found to be especially suitable for use in the preparation of aqueous dispersions of multi-polymer particles and details of this usage may be found in co-pending application PCT/AU82/00094.

The two component compounds of the invention may be used as amphipathic monomers in emulsion polymerisation reactions, making it possible to dispense with conventional surfactants. Such a use is described in co-pending PCT Application No. PCT/AU83/00090.

The invention is further described with reference to the following examples in which all parts are expressed by weight.

EXAMPLE 1

Preparation of a two component compound according to the invention wherein the hydrophilic component comprises 25 units of ethylene oxide per molecule and the unsaturated compound is eugenol.

164 g (1.0 mole) of eugenol was charged to a 2 litre stainless steel autoclave fitted with a rotary stirrer. The autoclave was purged with nitrogen and then sodium hydroxide (4.0 g, 0.1 mole) in water (10 ml) was added as catalyst. The autoclave was again purged with nitrogen. The autoclave and contents were heated to 140° C. and a vacuum established in the head space using a water pump. By this procedure the water content of the eugenol was reduced to a low value (0.1%) within about 1 hour. Ethylene oxide (1100 g, 25.0 mole) was then added to the autoclave over a period of about 4 hours, the temperature being maintained at 140°±5° by means of a cooling coil fitted to the autoclave. The maximum pressure developed during the run was 300 kPa. After the addition was complete, the autoclave was maintained at 140° for 1 hour to allow the ethylene oxide to react fully. The product was cooled to 75°, neutralised with dilute phosphoric acid solution, the water was stripped off under reduced pressure, and the product filtered. The final product was an off-white waxy solid.

EXAMPLE 2

Preparation of a two component compound according to the invention wherein the hydrophilic component comprises 35 units of ethylene oxide per molecule, the unsaturated compound is trimethylolpropane diallyl ether and the lipophilic component additionally comprises two units of butylene oxide per molecule.

169 g (0.79 mole) of trimethylolpropane diallyl ether was charged to an autoclave as described in Example 1. This was purged and catalysed as described in Example 1. After dehydration, the autoclave was cooled to and held at 110°±3° while 114 g (1.58 mole) of butylene oxide was added over period of 0.5 hour. The contents were held at 110° for 12 hours for complete reaction of the butylene oxide. The contents were then heated to 140° and 1217 g (27.7 mole) of ethylene oxide was added over a period of 4 hours keeping the temperature at 140°±5°. The reaction was continued for an hour and the product recovered as described in Example 1.

EXAMPLE 3

Preparation of a two component compound according to the invention wherein the hydrophilic component comprises 45 units of ethylene oxide per molecule, the unsaturated compound is pentaerythritol triallyl ether and the lipophilic component additionally comprises two units of propylene oxide per molecule.

Example 2 was repeated except that the following materials and quantities were used in order;

| pentaerythritol triallyl ether | 174 g (0.68 mole) |
| propylene oxide | 79 g (1.36 mole) |
| ethylene oxide | 1345 g (30.6 mole) |

EXAMPLES 4–9

Preparation of two component compounds according to the invention wherein the hydrophilic and lipophilic components are as set out below. The method of preparations is as set out in Example 2.

| Example No. | Hydrophilic Component | Lipophilic Component | MW of lipophilic Component |
| --- | --- | --- | --- |
| 4 | 35 units of ethylene oxide. | pentaerythritol triallyl ether + 2 units of butylene oxide | 450 |
| 5 | 25 units of ethylene oxide. | pentaerythritol triallyl ether + 2 units of butylene oxide | 450 |
| 6 | 50 units of ethylene oxide. | pentaerythritol triallyl ether + 2 units of butylene oxide | 450 |
| 7 | 4 units of ethylene oxide. | pentaerythritol triallyl ether + 2 units of butylene oxide | 450 |
| 8 | 35 units of ethylene oxide. | trimethylol propane diallyl ether + 2 units of propylene oxide. | 360 |
| 9 | 45 units of ethylene oxide. | trimethylol propane diallyl ether + 2 units of propylene oxide. | 360 |

We claim:

1. A non-ionic chemical compound having both hydrophilic and lipophilic components, the hydrophilic component comprising a polyalkylene oxide chain and the lipophilic component comprising at least one ethylenic double bond, characterised in that
   (a) the hydrophilic component comprises at least two ethylene oxide units
   (b) the lipophilic component has a molecular weight of 1000 maximum and comprises an entity derived from an unsaturated compound selected from the group consisting of pentaerythritol triallyl ether and trimethylolpropane diallyl ether; and
   (c) the compound has an HLB value of below 8.

2. A non-ionic chemical compound according to claim 1, characterised in that the lipophilic component is comprised entirely of an unsaturated compound selected from the group consisting of pentaerythritol triallyl ether and trimethylolpropane diallyl ether.

* * * * *